US008002822B2

(12) United States Patent
Glocker et al.

(10) Patent No.: US 8,002,822 B2
(45) Date of Patent: Aug. 23, 2011

(54) RADIOPAQUE COATING FOR BIOMEDICAL DEVICES

(75) Inventors: David A. Glocker, West Henrietta, NY (US); Mark M. Romach, Spencerport, NY (US)

(73) Assignee: Isoflux, Inc., Rochester, NY (US)

( * ) Notice: Subject to any disclaimer, the term of this patent is extended or adjusted under 35 U.S.C. 154(b) by 474 days.

(21) Appl. No.: 11/087,909

(22) Filed: Mar. 23, 2005

(65) Prior Publication Data

US 2005/0187466 A1 Aug. 25, 2005

Related U.S. Application Data

(63) Continuation-in-part of application No. 11/040,433, filed on Jan. 21, 2005, now abandoned.

(60) Provisional application No. 60/555,721, filed on Mar. 23, 2004, provisional application No. 60/579,577, filed on Jun. 14, 2004, provisional application No. 60/538,749, filed on Jan. 22, 2004.

(51) Int. Cl.
*A61F 2/82* (2006.01)
(52) U.S. Cl. ...................... 623/1.46; 623/1.42
(58) Field of Classification Search .................. 623/1.34, 623/1.12–1.2, 1.42, 1.44–1.46
See application file for complete search history.

(56) References Cited

U.S. PATENT DOCUMENTS

| 4,236,994 A * | 12/1980 | Dugdale ................ 204/298.09 |
| 4,440,178 A | 4/1984 | Bussard et al. |
| 4,603,704 A | 8/1986 | Mund et al. |
| 4,611,604 A | 9/1986 | Botvidsson et al. |
| 4,784,161 A | 11/1988 | Skalsky et al. |
| 4,844,099 A | 7/1989 | Skalsky et al. |
| 4,934,881 A | 6/1990 | Tsujimura et al. |
| 5,282,844 A | 2/1994 | Stokes et al. |
| 5,282,861 A | 2/1994 | Kaplan |
| 5,607,463 A | 3/1997 | Schwartz et al. ................ 623/1 |
| 5,630,840 A * | 5/1997 | Mayer ........................ 623/66.1 |
| 5,669,909 A | 9/1997 | Zdeblick et al. |
| 5,824,045 A | 10/1998 | Alt .................................... 623/1 |
| 5,858,556 A * | 1/1999 | Eckert et al. ................... 428/586 |
| 5,972,027 A * | 10/1999 | Johnson ....................... 623/1.42 |
| 5,984,967 A | 11/1999 | Zdeblick et al. |
| 5,991,667 A | 11/1999 | Feith |
| 6,063,442 A | 5/2000 | Cohen et al. |
| 6,099,561 A | 8/2000 | Alt ............................... 623/1.44 |

(Continued)

FOREIGN PATENT DOCUMENTS

JP  4620109 B2  1/2011

(Continued)

OTHER PUBLICATIONS

John A. Thornton, High Rate Thick Film Growth, 1977, pp. 239-260, Annual Reviews, Inc.

(Continued)

*Primary Examiner* — Thomas J Sweet
*Assistant Examiner* — Megan Wolf
(74) *Attorney, Agent, or Firm* — Heslin Rothenberg Farley & Mesiti, P.C.

(57) ABSTRACT

A medical device has a porous radiopaque coating that can withstand the high strains inherent in the use of such devices without delamination. A coating of Ta is applied to a medical device, such as a stent, by vapor deposition so that the thermomechanical properties of the stent are not adversely affected. The coating preferable has high emissivity.

30 Claims, 9 Drawing Sheets

U.S. PATENT DOCUMENTS

| | | | |
|---|---|---|---|
| 6,110,204 A * | 8/2000 | Lazarov et al. | 623/11.11 |
| 6,174,329 B1 | 1/2001 | Callol et al. | |
| 6,261,322 B1 | 7/2001 | Despres, III et al. | |
| 6,293,966 B1 | 9/2001 | Frantzen | |
| 6,312,456 B1 | 11/2001 | Kranz et al. | |
| 6,334,871 B1 | 1/2002 | Dor et al. | |
| 6,355,058 B1 | 3/2002 | Pacetti et al. | |
| 6,361,557 B1 | 3/2002 | Gittings et al. | |
| 6,375,655 B1 | 4/2002 | Zdeblick et al. | |
| 6,387,121 B1 | 5/2002 | Alt | 623/1.15 |
| 6,402,777 B1 | 6/2002 | Globerman et al. | |
| 6,455,173 B1 * | 9/2002 | Marijnissen et al. | 428/623 |
| 6,464,723 B1 | 10/2002 | Callol | |
| 6,471,721 B1 | 10/2002 | Dang | |
| 6,497,671 B2 | 12/2002 | Ferrera et al. | |
| 6,503,271 B2 | 1/2003 | Duerig et al. | |
| 6,540,774 B1 | 4/2003 | Cox | |
| 6,554,854 B1 | 4/2003 | Flanagan | |
| 6,585,757 B1 | 7/2003 | Callol | |
| 6,613,091 B1 | 9/2003 | Zdeblick et al. | |
| 6,616,765 B1 | 9/2003 | Castro et al. | |
| 6,620,192 B1 | 9/2003 | Jalisi | |
| 6,635,082 B1 | 10/2003 | Hossainy et al. | |
| 6,638,301 B1 * | 10/2003 | Chandrasekaran et al. | 623/1.34 |
| 6,641,607 B1 | 11/2003 | Hossainy et al. | |
| 6,645,206 B1 | 11/2003 | Zdeblick et al. | |
| 6,652,579 B1 | 11/2003 | Cox et al. | |
| 7,488,343 B2 * | 2/2009 | O'Brien et al. | 623/1.15 |
| 2001/0032005 A1 | 10/2001 | Gelb et al. | |
| 2001/0032013 A1 * | 10/2001 | Marton | 623/1.15 |
| 2002/0049402 A1 * | 4/2002 | Peacock et al. | 604/8 |
| 2002/0144903 A1 | 10/2002 | Kim et al. | |
| 2004/0039438 A1 * | 2/2004 | Alt | 623/1.15 |
| 2005/0266040 A1 | 12/2005 | Gerberding | 424/423 |
| 2006/0276885 A1 | 12/2006 | Lye et al. | |

FOREIGN PATENT DOCUMENTS

| | | |
|---|---|---|
| WO | 0155473 A1 | 8/2001 |
| WO | 0187371 A2 | 11/2001 |

OTHER PUBLICATIONS

Dean W. Matson, Edwin D. McClanahan, Sabrina L. Lee and Donald Windover, Properties of Thick Sputtered Ta Used for Protective Gun Tube Coating, Surface and Coatings Technology, 2001, pp. 344-350.

Nanobumps Enhance Implants, R&D Magazine, Jan. 2004, p. 46, US.

W. D. Westwood, Calculation of Deposition Rates in Diode Sputtering Systems, J. ac. Sci. Technol., pp. 1-9, Jan./Feb. 1978.

Precision Silver Coating, www.medicalsysforindustry.com/page65.htm.

Precision Gold Coating, www.medicalsysforindustry.com/teflonmetal.htm.

Precision Titanium Coating, www.medicalsysforindustry.com/page66.htm.

4 pages from www.devicelink.com/mddi/archive/99/05/011.html; Medical Device & Diagnostic Industry Magazine, MDDI Article Index; May 1999 column, "Radiopaque Coatings".

Thorton, John A., Influence of apparatus geometry and deposition conditions on the structure and topography of thick sputtered coatings, J. Vac. Sci. Technol., vol. 11, No. 4, Jul./Aug. 1974.

Pellegrino, Brian E., United States Patent and Trademark Office Examiner, Final Office Action dated Sep. 21, 2009, U.S. Appl. No. 11/087,909, filed Mar. 23, 2005, entitled Radiopacque Coating for Biomedical Devices.

Japanese Office Action translation for corresponding Japanese Application No. 2007-516591.

* cited by examiner

Figure 1

Prior Art

RADIOPAQUE COATING FOR BIOMEDICAL DEVICES

CROSS REFERENCE TO RELATED APPLICATION

This application claims the benefit of U.S. Provisional Application Nos. 60/555,721 and 60/579,577 filed Mar. 23, 2004 and Jun. 14, 2004, respectively, and is a continuation-in-part of U.S. patent application Ser. No. 11/040,433 filed Jan. 21, 2005 now abandoned that claims the benefit of U.S. Provisional Application No. 60/538,749 filed Jan. 22, 2004; the entire disclosures of which are incorporated herein by reference in their entirety for any and all purposes.

TECHNICAL FIELD

The present invention relates to medical devices.

BACKGROUND

Stents have become extremely important devices in the treatment of cardiovascular disease. A stent is a small mesh "scaffold" that can be positioned in an artery to hold it open, thereby maintaining adequate blood flow. Typically a stent is introduced into the patient's system through the brachial or femoral arteries and moved into position using a catheter and guide wire. This minimally invasive procedure replaces surgery and is now used widely because of the significant advantages it offers for patient care and cost.

In order to deploy a stent, it must be collapsed to a fraction of its normal diameter so that it can be manipulated into the desired location. Therefore, many stents and guide wires are made of an alloy of nickel and titanium, known as nitinol, which has the unusual properties of superelasticity and shape memory. Both of these properties result from the fact that nitinol exists in a martensitic phase below a first transition temperature, known as $M_f$ and an austenitic phase above a second transition temperature, known as $A_f$. Both $M_f$ and $A_f$ can be manipulated through the ratio of nickel to titanium in the alloy as well as thermal processing of the material. In the martensitic phase nitinol is very ductile and easily deformed, while in the austenitic phase it has a high elastic modulus. Applied stresses produce some martensitic material at temperatures above $A_f$ and when the stresses are removed the material returns to its original shape. This results in a very springy behavior for nitinol, referred to as superelasticity or pseudoelasticity. Furthermore, if the temperature is lowered below $M_f$ and the nitinol is deformed, when the temperature is raised above $A_f$ it will recover its original shape. This is described as shape memory.

Stents having superelasticity and shape memory can be compressed to small diameters, moved into position, and deployed so that they recover their full size. By choosing an alloy composition having an $A_f$ below normal body temperature, the stent will remain expanded with significant force once in place. Remarkably, during this procedure the nitinol must typically withstand strain deformations of as much as 8%.

Stents and similar intraluminal devices can also be made of materials like stainless steel and other metal alloys. Although they do not exhibit shape memory or superelasticity, stents made from these materials also must undergo significant strain deformations in use.

Figure 1:
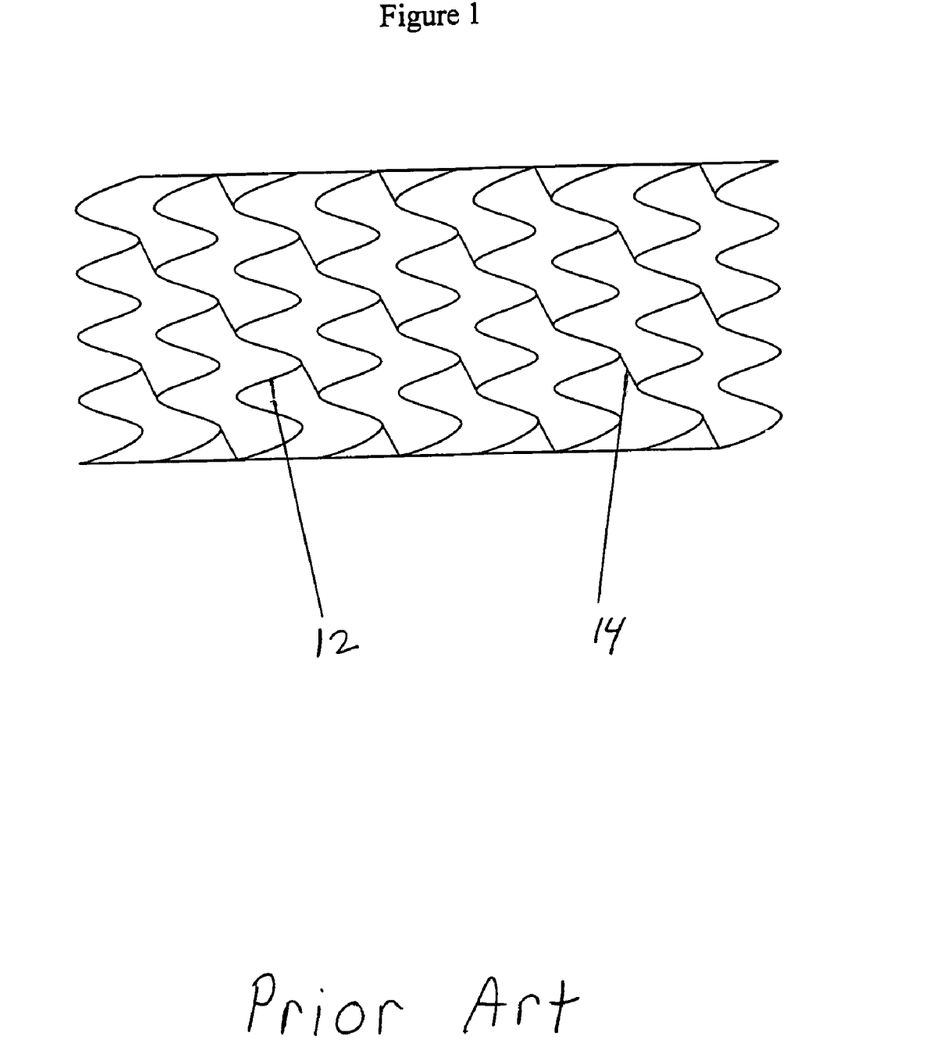
FIG. 1 illustrates a stent found in the prior art.

FIG. 1 illustrates one of many stent designs that are used to facilitate this compression and expansion. This design uses ring shaped "struts" 12, each one having corrugations that allow it to be collapsed to a small diameter. Bridges 14, a.k.a. nodes, that also must flex in use connect the struts. Many other types of expandable geometries, such as helical spirals, braided and woven designs and coils, are known in the field and are used for various purposes.

One disadvantage of stents made from nitinol and many other alloys is that the metals used often have low atomic numbers and are, therefore, relatively poor X-ray absorbers. Consequently, stents of typical dimensions are difficult or impossible to see with X-rays when they are being manipulated or are in place. Such devices are called radio transparent. There are many advantages that would result from being able to see a stent in an X-ray. For example, radiopacity, as it is called, would result in the ability to precisely position the stent initially and in being able to identify changes in shape once it is in place that may reflect important medical conditions.

Many methods are described in the prior art for rendering stents or portions of stents radiopaque. These include filling cavities on the stent with radiopaque material (U.S. Pat. Nos. 6,635,082; 6,641,607), radiopaque markers attached to the stent (U.S. Pat. Nos. 6,293,966; 6,312,456; 6,334,871; 6,361,557; 6,402,777; 6,497,671; 6,503,271; 6,554,854), stents comprised of multiple layers of materials with different radiopacities (U.S. Pat. Nos. 6,638,301; 6,620,192), stents that incorporate radiopaque structural elements (U.S. Pat. Nos. 6,464,723; 6,471,721; 6,540,774; 6,585,757; 6,652,579), coatings of radiopaque particles in binders (U.S. Pat. No. 6,355,058), and methods for spray coating radiopaque material on stents (U.S. Pat. No. 6,616,765).

All of the prior art methods for imparting radiopacity to stents significantly increase the manufacturing cost and complexity and/or render only a small part of the stents radiopaque. The most efficient method would be to simply apply a conformal coating of a fully dense radiopaque material to all surfaces of the stent. The coating would have to be thick enough to provide good X-ray contrast, biomedically compatible and corrosion resistant. More challenging, however, it would have to be able to withstand the extreme strains in use without cracking or flaking and would have to be ductile enough that the important thermomechanical properties of the stent are preserved. In addition, the coatings must withstand the constant flexing of the stent that takes place because of the expansion and contraction of blood vessels as the heart pumps.

Physical vapor deposition techniques, such as sputtering, thermal evaporation and cathodic arc deposition, can produce dense and conformal coatings of radiopaque materials like gold, platinum, tantalum, tungsten and others. Physical vapor deposition is widely used and reliable. However, coatings produced by these methods do not typically adhere well to substrates that undergo strains of up to 8% as required in this application. This problem is recognized in U.S. Pat. No. 6,174,329, which describes the need for protective coatings over radiopaque coatings to prevent the radiopaque coatings from flaking off when the stent is being used.

Another important limitation of radiopaque coatings deposited by physical vapor deposition is the temperature sensitivity of nitinol and other stent materials. As mentioned, shape memory biomedical devices are made with values of $A_f$ close to but somewhat below normal body temperature. If nitinol is raised to too high a temperature for too long its $A_f$ value will rise and sustained temperatures above 300-400 C will adversely affect typical $A_f$ values used in stents. Likewise, if stainless steel is raised to too high a temperature, it can lose its temper. Other stent materials would also be adversely affected. Therefore, the time-temperature history of a stent during the coating operation is critical. In the prior art it is customary to directly control the temperature of a substrate in such a situation, particularly one with a very low thermal mass such as a stent. This is usually accomplished by placing the substrate in thermal contact with a large mass, or heat sink, whose temperature is controlled. This process is known as controlling the temperature directly or direct control. Because of its shape and structure, controlling the temperature of a stent directly during coating would be a challenging task. Moreover, the portion of the stent in contact with the heat sink would receive no coating and the resulting radiographic image could be difficult to interpret.

Accordingly, there is a need in the art for biomedical devices having radiopaque coatings thick enough to provide good x-ray contrast, biomedical compatibility and corrosion resistance. Further, the coating needs to withstand the extreme strains in use without cracking or flaking and be sufficiently ductile so that the thermo-mechanical properties of the device are preserved.

SUMMARY

The present invention is directed towards a medical device having a radiopaque outer coating that is able to withstand the strains produced in the use of the device without delamination.

A medical device in accordance with the present invention can include a body at least partially comprising a nickel and titanium alloy and a Ta coating on at least a portion of the body; wherein the Ta coating is sufficiently thick so that the device is radiopaque and the Ta coating is able to withstand the strains produced in the use of the device without delamination. The Ta coating can consist primarily of the bcc crystalline phase. The coating thickness is preferably between approximately 3 and 10 microns. The device can be a stent or a guidewire, for example. The coating preferably is porous.

A process for depositing a Ta layer on a medical device consisting of the steps of: maintaining a background pressure of inert gas in a sputter coating system containing a Ta sputter target; applying a voltage to the Ta target to cause sputtering; and sputtering for a period of time to produce the desired coating thickness; wherein the Ta layer preferably has an emissivity in the visible spectrum of at least 80%. The device preferably is not directly heated or cooled and the equilibrium temperature of the device during deposition is controlled indirectly by the process. The equilibrium temperature preferably is between 150° and 450° C. A voltage, ac or dc, can be applied steadily or in pulses to the medical device during the process. An initial high voltage, preferably between 300 and 500 volts, can be applied to preclean the device for a first period of time, preferably between 1 minute and 20 minutes. A second, lower voltage, preferably between 50 and 200 volts, can be applied for a period of time, preferably between 1 and 3 hours. Preferably, the inert gas is from the group comprising Ar, Kr and Xe. Preferably, the voltage on the target(s) produces a deposition rate of 1 to 4 microns per hour. The target preferably is a cylinder or a plate.

A medical device comprises a body having an outer layer and a radiopaque coating on at least a portion of the outer layer; wherein the coating is applied using a physical vapor deposition technique.

BRIEF DESCRIPTION OF THE DRAWINGS

These and other features, aspects and advantages of the present invention will become better understood with regard to the following description, appended claims, and accompanying drawings where:

DESCRIPTION

Tantalum has a high atomic number and is also biomedically inert and corrosion resistant, making it an attractive material for radiopaque coatings in this application. It is known that 3 to 10 microns of Ta is sufficiently thick to produce good X-ray contrast. However, because Ta has a melting point of almost 3000 C., any coating process must take place at a low homologous temperature (the ratio of the deposition temperature to the melting temperature of the coating material in degrees Kelvin) to preserve the $A_f$ values of the stents as described previously. It is well known in the art of physical vapor deposition that low homologous coating temperatures often result in poor coating properties. Nevertheless, we have unexpectedly found that radiopaque Ta coatings deposited under the correct conditions are able to withstand the strains inherent in stent use without unacceptable flaking.

Still more remarkable is the fact that we can deposit these adherent coatings at high rates with no direct control of the stent temperature without substantially affecting $A_f$. Since normal body temperature is 37 C., the $A_f$ value after coating should be less than this temperature to avoid harming the thermomechanical properties of the nitinol. The lower $A_f$ is after coating the more desirable the process is.

For a thermally isolated substrate, the equilibrium temperature will be determined by factors such as the heat of condensation of the coating material, the energy of the atoms impinging on the substrate, the coating rate, the radiative cooling to the surrounding chamber and the thermal mass of the substrate. It is surprising that this energy balance permits high-rate coating of a temperature sensitive low mass object such as a stent without raising the temperature beyond acceptable limits. Eliminating the need to directly control the temperature of the stents significantly simplifies the coating operation and is a particularly important consideration for a manufacturing process.

This patent relates to coatings that render biomedical devices including intraluminal biomedical devices radiopaque and that withstand the extremely high strains inherent in the use of such devices without unacceptable delamination. Specifically, it relates to coatings of Ta having these properties and methods for applying them that do not adversely affect the thermomechanical properties of stents.

Figure 2:
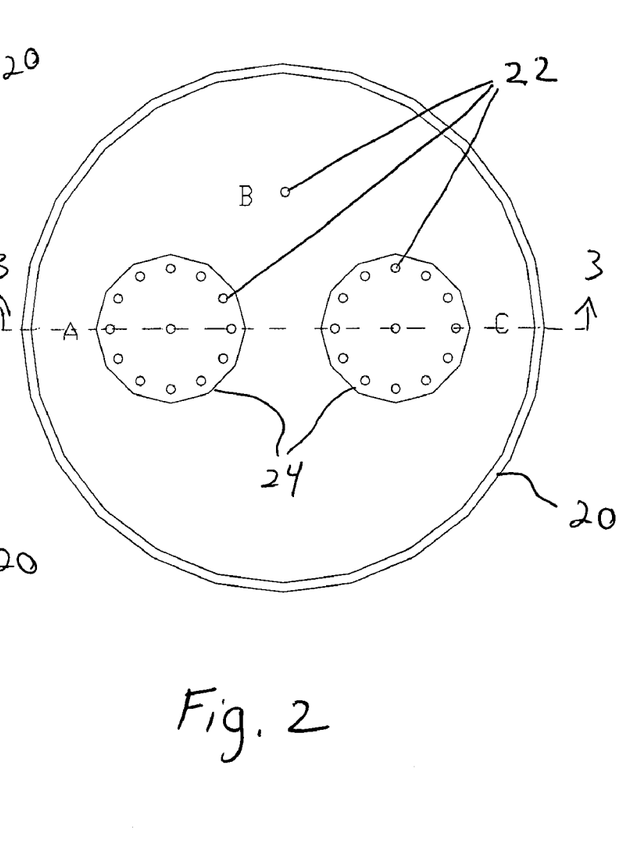
FIG. 2 is a top view of a Ta target surrounding stents.
Figure 3:
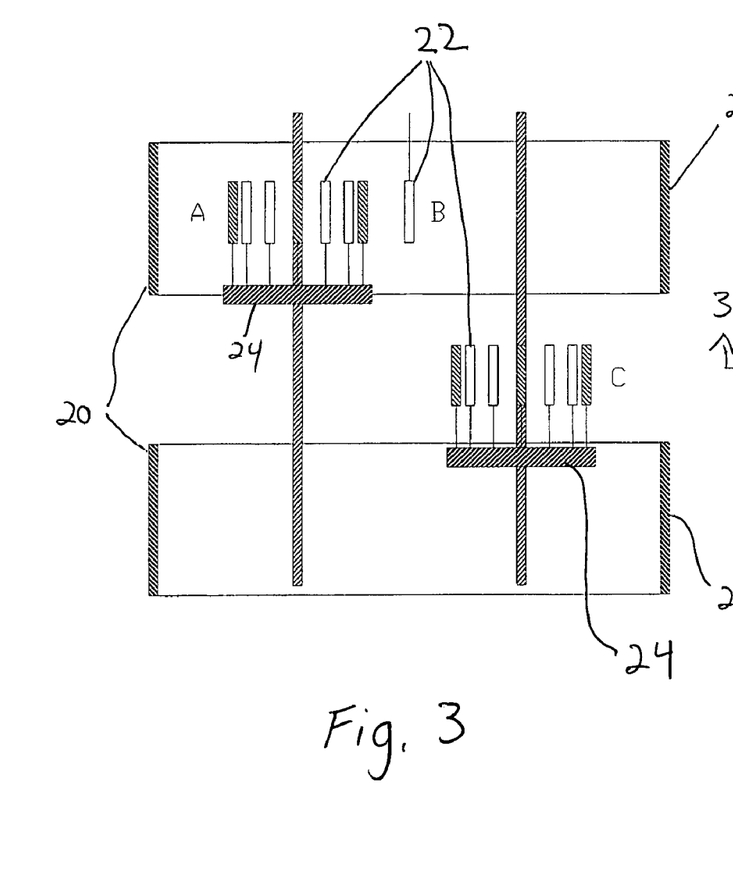
FIG. 3 is a side cross-sectional view of the target surrounding stents of FIG. 2.

An unbalanced cylindrical magnetron sputtering system described in U.S. Pat. No. 6,497,803 B2, which is incorporated herein by reference, was used to deposit the coatings. FIGS. 2 and 3 illustrate the setup. Two Ta targets 20, each 34 cm in diameter and 10 cm high, separated by 10 cm, were used. They were driven with either DC power or AC power at 40 kHz. Xenon or krypton was used as the sputter gas. The total power to both cathodes was either 2 kW or 4 kW and a bias of either −50 V or −150 V was applied to the stents during coating. Other devices well known to those in the art, such as vacuum pumps, power supplies, gas flow meters, pressure measuring equipment and the like, are omitted from FIGS. 2 and 3 for clarity.

In each coating run, stents 22 were placed at one of three positions, as shown in FIGS. 2 and 3:

Position A—The stents were held on a 10 cm diameter fixture 24 that rotated about a vertical axis, which was approximately 7 cm from the cathode centerline. The vertical position of the stents was in the center of the upper cathode. Finally, each stent was periodically rotated about its own vertical axis by a small "kicker", in a manner well known in the art.

Position B—The stents 22 were supported from a rotating axis that was approximately 7 cm from the chamber centerline. The vertical position of the stents was in the center of the upper cathode.

Position C—The stents 22 were on a 10 cm diameter fixture or plate 24 that rotated about a vertical axis, which was approximately 7 cm from the cathode centerline. The vertical position of the stents was in the center of the chamber, midway between the upper and lower cathodes. Finally, each stent was periodically rotated about its own vertical axis with a "kicker."

Prior to coating, the stents were cleaned with a warm aqueous cleaner in an ultrasonic bath. Crest 270 Cleaner (Crest Ultrasonics, Inc.) diluted to 0.5 pounds per gallon of water was used at a temperature of 55 C. This ultrasonic detergent cleaning was done for 10 minutes. The stents were then rinsed for 2 minutes in ultrasonically agitated tap water and 2 minutes in ultrasonically agitated de-ionized water. The stents were then blown dry with nitrogen and further dried with hot air. The manner in which the stents were cleaned was found to be very important. When the stents were cleaned ultrasonically in acetone and isopropyl alcohol, a residue could be seen on the stents that resulted in poor adhesion. This residue may be a consequence of material left after the electropolishing process, which is often done using aqueous solutions.

The Ta sputtering targets were preconditioned at the power and pressure to be used in that particular coating run for 10 minutes. During this step a shutter isolated the stents from the targets. This preheating allowed the stents to further degas and approach the actual temperature of the coating step. After opening the shutter, the coating time was adjusted so that a coating thickness of approximately 10 microns resulted. At a power of 4 kW the time was 2 hours and 15 minutes and at a power of 2 kW the time was 4 hours and 30 minutes. These are very acceptable coating rates for a manufacturing process. The stents were not heated or cooled directly in any way during deposition. Their time-temperature history was determined entirely by the coating process.

Figure 4:
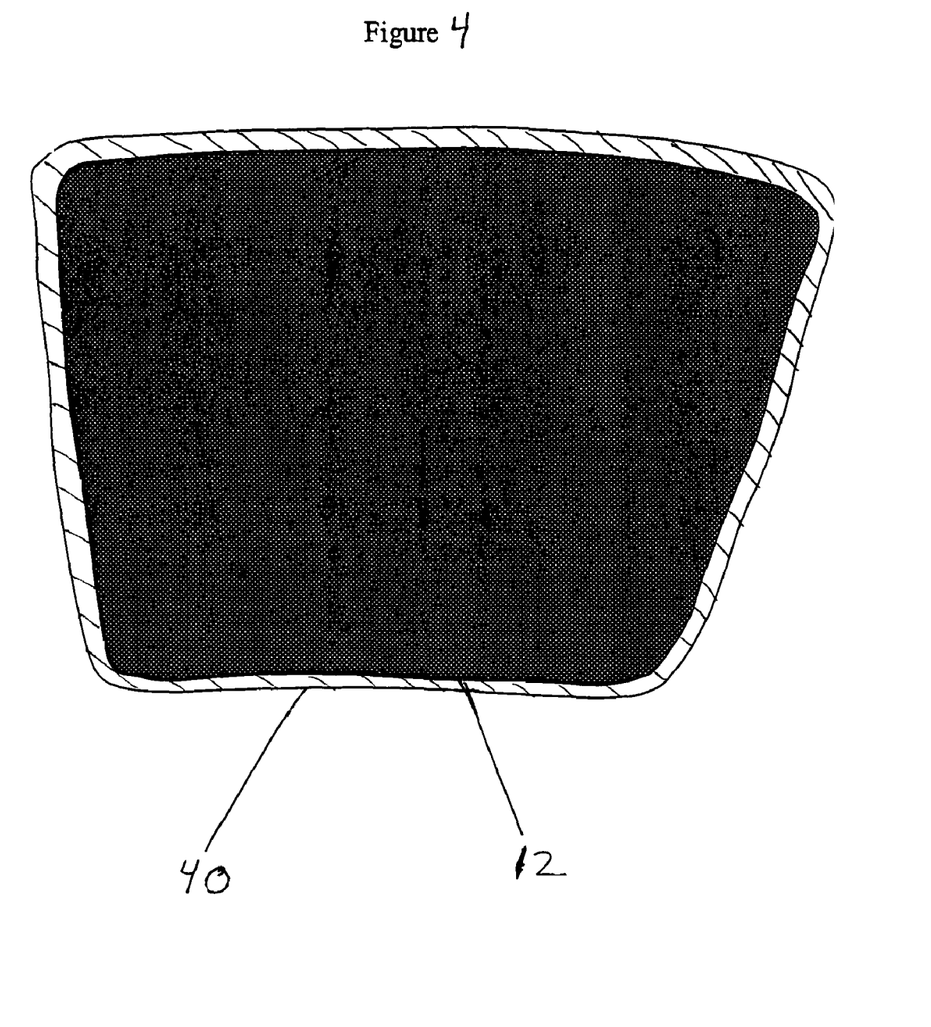
FIG. 4 illustrates a cross section of a conformal coating of Ta on a strut 12 of a stent.

FIG. 4 illustrates the cross section of a conformal coating of Ta 40 on a strut 12, shown approximately to scale for a 10-micron thick coating. Stents coated in this manner were evaluated in several ways. First, they were pressed into adhesive tape to see if there was any flaking or removal when the tape was peeled away. Next, the stents were flexed to their maximum extent and examined for flaking. In all cases this flexing was done at least three times and in some cases it was done as many as ten times. Finally, the $A_f$ values for the stents were measured by determining the temperature at which they recovered their original shape using a water bath.

Table 1 summarizes the results. The level of flaking and $A_f$ temperatures at positions A and B were very similar in the experiments and were averaged to produce the values shown. The level of flaking was ranked using the following procedure:

Level 5: Approximately 10% or more of the coated area flaked.

Level 4: Between approximately 5% and 10% of the coated area flaked.

Level 3: Between approximately 1% and 5% of the coated area flaked.

Level 2: Between approximately 0.1% and 1% of the coated area flaked.

Level 1: An occasional flake was observed, but less than approximately 0.1% of the coated area flaked.

Level 0: No flakes were observed.

Depending on the application, some level of flaking may be tolerated and we consider Level 2, Level 1 or Level 0 flaking acceptable.

TABLE 1

| Run No | Power | Gas | Bias | AC/DC | Flaking | Af | Appearance |
|---|---|---|---|---|---|---|---|
| 1 | 2 kW | Xe | 50 | AC | 5 | 29 | Dull mottled appearance |
| 2 | 2 kW | Kr | 150 | AC | 0 | 59 | Shiny metallic appearance |
| 3 | 4 kW | Kr | 50 | AC | 4 | 57 | Dull mottled appearance |
| 4 | 4 kW | Xe | 150 | AC | 0 | 60 | Shiny metallic appearance |
| 5 | 2 kW | Kr | 50 | DC | 0 | 23 | Black appearance |
| 6 | 2 kW | Xe | 150 | DC | 0 | 27 | Dull mottled appearance |
| 7 | 4 kW | Xe | 50 | DC | 4 | 32 | Shiny metallic appearance |
| 8 | 4 kW | Kr | 150 | DC | 1 | 38 | Shiny metallic appearance |

It can be seen from the results with respect to positions A and B that a major factor in determining adhesion is the bias voltage. A bias of −150 V produces much better adhesion overall than a bias of −50 V. This is consistent with many reports in the literature that higher substrate bias produces better adhesion in many applications. However, it also produces greater heating at a given power, as determined by the $A_f$ values.

Figure 5:
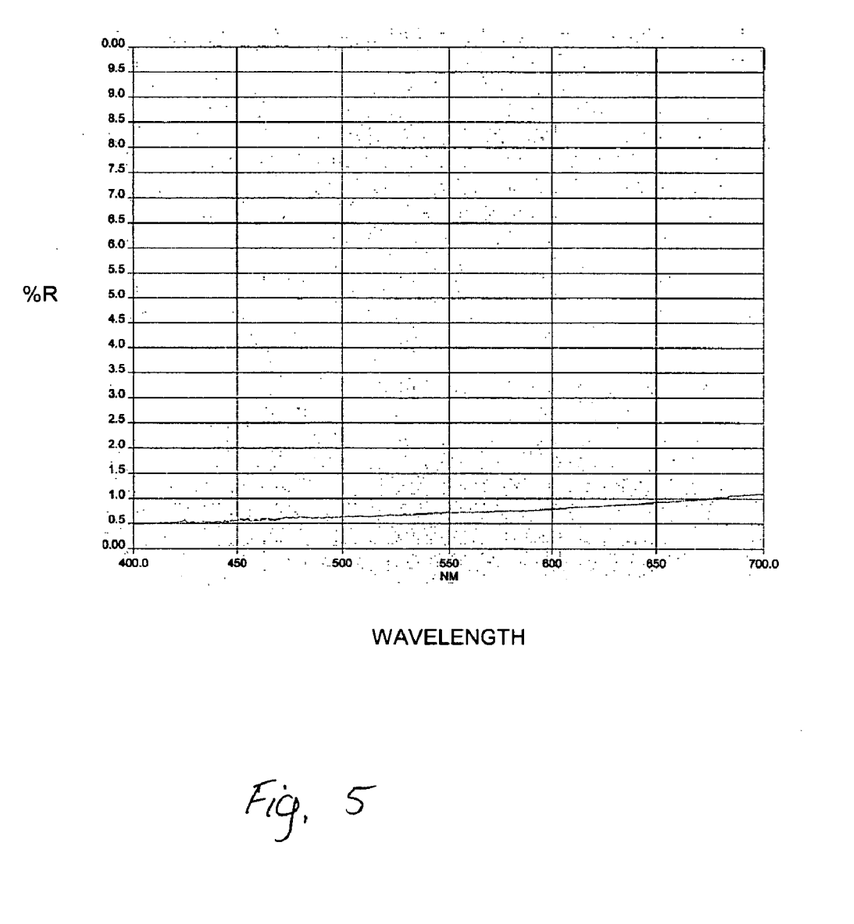
FIG. 5 is a graph showing the reflectance of a Ta coating made according to the present invention with respect to wavelength.

An obvious and important exception to the need for high bias to produce good adhesion is Run Number 5, which has both excellent adhesion and the lowest value for $A_f$ among the coatings. Moreover, the coating appearance of Run Number 5 was black, which could be appealing visually. This is indicative of a very high emissivity in the visible spectrum, characteristic of a so-called black body. As charted in FIG. 5, the reflectance was measured to be about 0.5% at a wavelength of 400 nm and rises to about 1.10% at 700 nm. This is an emissivity of approximately 99% or greater across the visible spectrum.

The combination of a very low $A_f$ and excellent adhesion is very surprising. Without being bound to this explanation, one possibility consistent with the observed results is that the coating is very porous. Low homologous temperatures (the ratio of the substrate temperature during coating to the melting point of the coating material, in degrees Kelvin) are known to produce open, columnar coating structures. The observed black appearance may be the result of an extremely porous coating. It is also known in the art that such morphology is also associated with very low coating stress, since the coating has less than full density. However, even if this explanation is correct, the excellent adhesion is very surprising. Typically such porous coatings have very poor adhesion and we were able to aggressively flex the coating with no indication of flaking.

Another possible consequence of the high emissivity of the coating is the fact that the radiative cooling of the stent during coating is more effective, thereby helping to maintain a low coating temperature.

Figure 6:
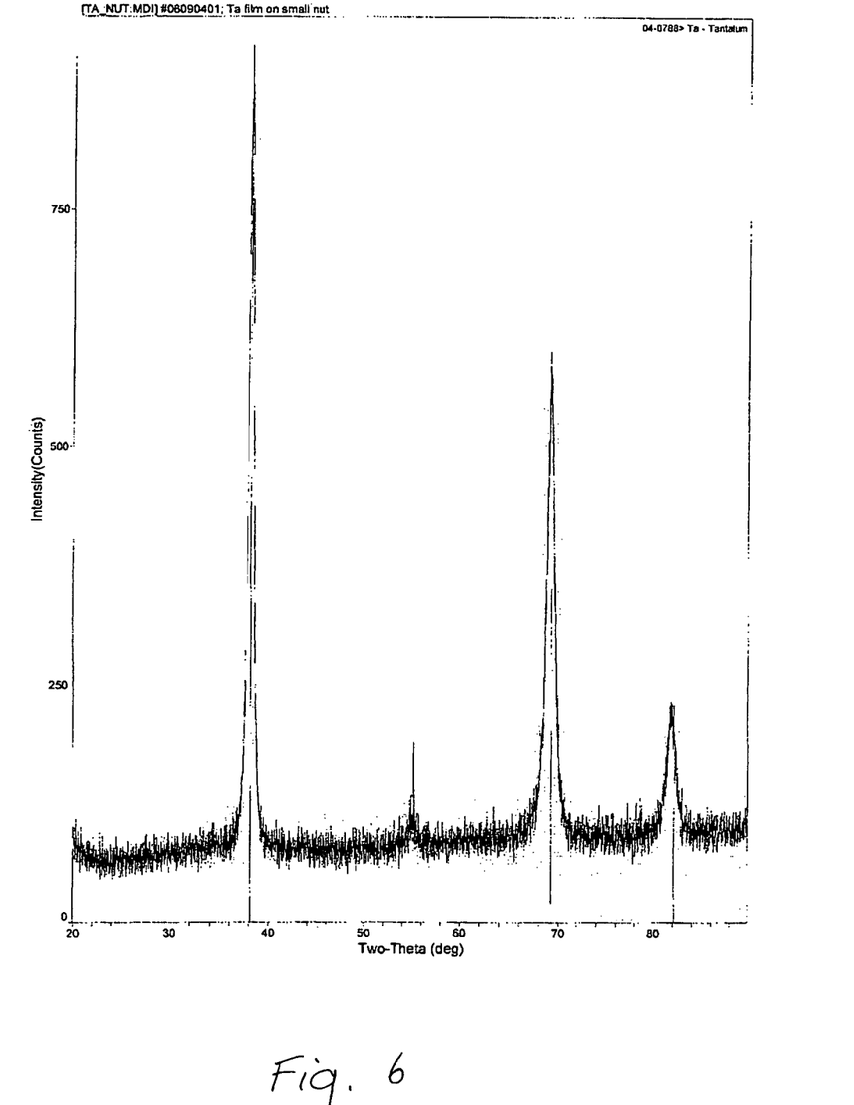
FIG. 6 is a graph showing the x-ray diffraction pattern of a Ta coating made according to the present invention.

Furthermore, as described in Utility patent application Ser. No. 11/040,433, which is incorporated herein by reference, sputtered Ta typically exists in one of two crystalline phases, either tetragonal (known as the beta phase) or body centered cubic (known as the alpha phase). The alpha phase of Ta is much more ductile than the beta phase and can withstand greater strains. Therefore, the alpha phase of Ta is more desirable in this application. FIG. 6 is an X-ray diffraction pattern of a coating made under the conditions of Run No. 5 described above, showing that the coating is alpha tantalum. It is known in the art that sputtering Ta in Kr or Xe with substrate bias can result in the alpha phase being deposited. See, for example, *Surface and Coatings Technology* 146-147 (2001) pages 344-350. However, there is nothing in the prior art or in our experience to suggest that alpha Ta coatings of 10 microns thickness can withstand the very high strains inherent in the use of stents without delamination and coating failure. There is also nothing in the prior art to suggest that alpha Ta can be deposited in such an open, porous structure.

An open, porous structure may have other advantages as well. For example, the microvoids in the coating would permit the incorporation of drugs or other materials that diff-use out over time. In the art, drug-eluting coatings on stents are presently made using polymeric materials. A porous inorganic coating would allow drug-eluting stents to be made without polymeric overcoats.

Surprisingly, the stents at position C all had adhesion equal to or better than the stents at positions A and B, regardless of conditions. Table 2 illustrates the surprising results. (NA indicates coating runs for which no data was taken at those positions.) The stents at position C always had very little or no flaking, even under coating conditions where stents in positions A or B had significant flaking. As can be seen from Table 2, this is true over a wide range of coating conditions. The $A_f$ values of the stents in position C were comparable to those in the other positions, and in the case of the AC coatings they were sometimes significantly lower. Stents in the C position that were sputter coated in Kr at a pressure of 3.4 mTorr, an AC power of 2 kW with −150 V bias (Run Nos. 2 and 3) had a metallic appearance and an $A_f$ between 38 and 42 C. Those coated in the C position using Kr at a pressure of 3.4 mTorr, a DC power of 2 kW and −50 V bias (Run No. 8) were black in appearance with an $A_f$ of only 24 C. An $A_f$ of 24 C is virtually unchanged from the $A_f$ values before coating. Both the metallic and the black samples had excellent adhesion. The fact that position C is preferable for adhesion and $A_f$ in virtually every case is unexpected.

TABLE 2

| Total Power | Gas | Bias | AC/DC | Position A | Position B | Position C |
|---|---|---|---|---|---|---|
| 2 kW | Xe | 50 | AC | Af = 29 C 5 | Af = 28 C 5 | Af = 30 C 0 |
| 2 kW | Kr | 150 | AC | Af = 59 C 0 | NA | Af = 42 C 0 |
| 2 kW | Kr | 150 | AC | Af = 52 C 0 | Af = 45 C 0 | Af = 38 C 0 |
| 4 kW | Kr | 50 | AC | Af = 56 C 4 | Af = 58 C 4 | NA |
| 4 kW | Kr | 150 | AC | Af > 55 C 0 | Af > 55 C 0 | NA |
| 4 kW | Kr | 150 | AC | NA | Af > 55 C 0 | NA |
| 4 kW | Xe | 150 | AC | NA | Af > 55 C 0 | NA |
| 2 kW | Kr | 50 | DC | Af = 25 C 0 | Af = 22 C 0 | Af = 24 C 0 |
| 4 kW | Xe | 150 | DC | Af = 37 C 1 | Af = 37 C 5 | Af = 38 C 0 |
| 4 kW | Xe | 50 | DC | Af = 32 C 3 | Af = 33 C 5 | Af = 31 C 1 |
| 4 kW | Kr | 150 | DC | Af = 38 C 1 | Af = 38 C 0 | Af = 49 C 0 |
| 2 kW | Xe | 150 | DC | Af = 25 C 0 | Af = 29 C 0 | Af = 25 C 1 |

Stents in position C receive a generally more oblique and lower energy coating flux than stents in positions A or B. By an oblique coating flux we mean that the majority of the depositing atoms arrive in directions that are not generally perpendicular to the surface being coated. Some of the atoms arriving at the surfaces of the stents in position C from the upper and lower targets will have done so without losing significant energy or directionality because of collisions with the background sputter gas. Those atoms, most of which will come from portions of the targets close to the stents as seen in FIGS. 2 and 3, will create an oblique coating flux. Other atoms will undergo several collisions with the background gas and lose energy and directionality before arriving at the substrate surfaces. Those atoms, which will generally come from portions of the targets at greater distances, will form a low energy coating flux. Westwood has calculated ("Calculation of deposition rates in diode sputtering systems," W. D. Westwood, Journal of Vacuum Science and Technology, Vol. 15 page 1 (1978)) that the average distance a Ta atom goes in Ar at 3.4 mTorr before its energy is reduced to that of the background gas is between about 15 and 30 cm. (The distance would be somewhat less in Kr and the exact value depends on the initial energy of the Ta atom.) Because our cylindrical targets have an inside diameter of approximately 34 cm, substrates placed in the planes of the targets (positions A and B) receive a greater number of high energy, normal incidence atoms than those placed between the targets (position C).

The geometry of the cylindrical magnetron arrangement shown in FIGS. 2 and 3 assures that atoms arriving at the surface of the stents in position C will do so either at relatively oblique angles or with relatively low energy. Referring to FIGS. 2 and 3, when the stents are close to the targets, where the arriving Ta atoms have lost little energy, the atoms arrive at oblique angles. And when the stents move closer to the center of the chamber where the arrival angles are less oblique, they are farther from the target surface so that the arriving Ta atoms have lost energy through gas collisions.

It is widely known in the art that when the atoms in a PVD process arrive with low energies or at oblique angles to the substrate surface, the result is a coating that is less dense than a coating made up of atoms arriving at generally normal incidence or with higher energies. The black appearance of the low power DC coatings deposited with low substrate bias (Run 5 in Table 1 and Run 8 in Table 2) may be the result of considerable coating porosity. Normally low-density PVD coatings are not desirable, but we have found that conditions that result in relatively low density or porous coatings produce very desirable results in this application.

Figure 7:
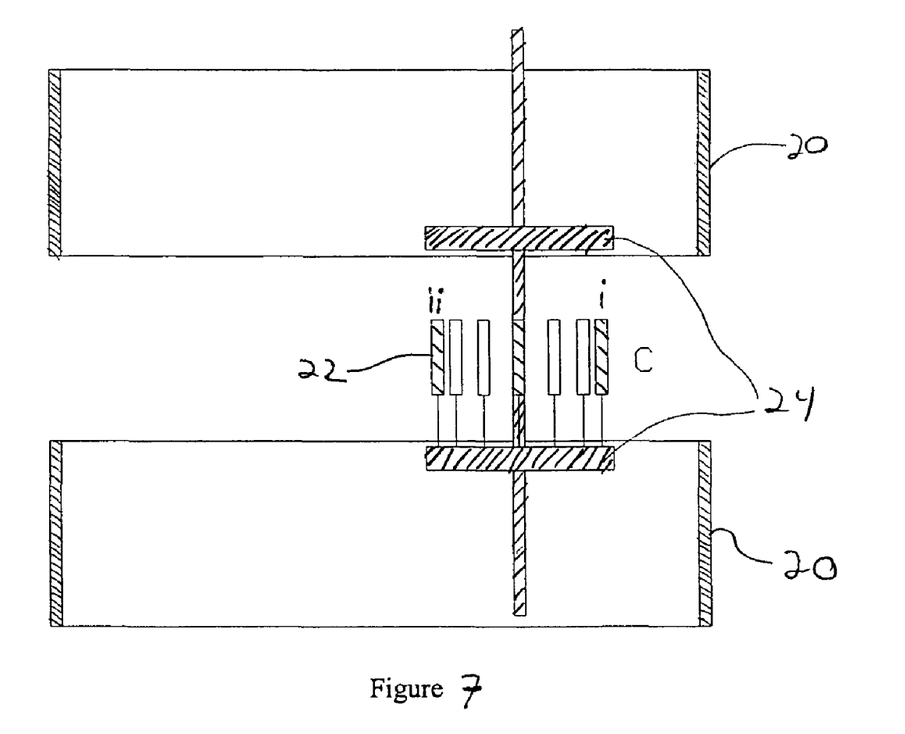
FIG. 7 is a side cross-sectional view of the target surrounding stents in position C of FIG. 3 with a plate above the stents.

Further evidence of the importance of the coating geometry is seen in the following experiment. A number of coatings were done in Kr at a pressure of 3.4 mTorr, a DC power of 2 kW and a bias of −50 V using the fixture shown in FIGS. 2 and 3 in position C. As before, the stents were rotating about the vertical rod as well as about their own vertical axes. The coated stents made this way were matte black at the bottom but had a slightly shinier appearance at the top. In contrast, when coatings were done on stents 22 under identical conditions, except that a second plate 24 was placed above the stents as shown in FIG. 7, the stents were a uniform black from bottom to top.

The non-uniformity in appearance that resulted with the fixturing shown in FIGS. 2 and 3 in position C indicates that the coating structure depends on the details of how the stents and sputter targets are positioned relative to one another. As discussed earlier, when the stents are in position C1 in FIG. 3, they receive very oblique incidence material from portions of the targets that are close, while the coating material that arrives from other portions of the target has to travel farther. Therefore, all of the coating flux has arrived at high angles or has traveled a considerable distance and has lost energy and directionality through collisions with the sputtering gas. When the stents are in position C2 in FIG. 3, however, they receive a somewhat less oblique coating from all directions. In the configuration shown in FIG. 3, position C the bottoms of the stents are shielded from the more direct flux from the bottom target by the plate that holds them, but the tops of the stents are not similarly shielded from the more direct flux coming from the top target. By adding the plate above the stents shown in FIG. 7, the more direct coating flux is shielded at all points on the stents and the coating material either arrives at relatively oblique incidence or after scattering from the background gas and losing energy and directionality. The plate above the stents restores the symmetry of the situation and the coatings on the stents become uniformly black overall.

Figures 8, 9:
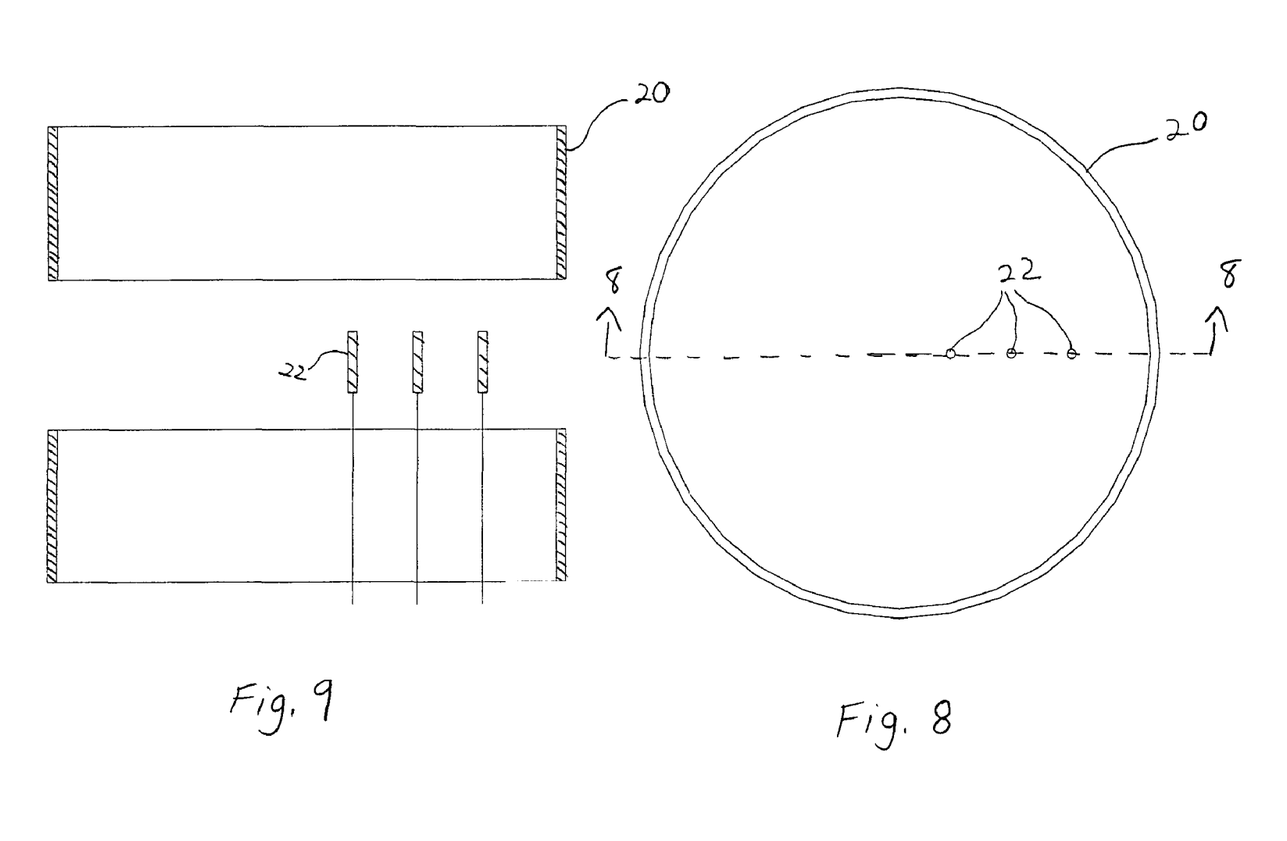
FIG. 8 is a top view of a Ta target surrounding stents.
FIG. 9 is a side cross-sectional view of the target surrounding stents of FIG. 8.

Other methods of positioning and moving the substrates within the chamber can also produce results similar to those described above and are within the scope of the invention. In another experiment three stents were located as shown in FIGS. 8 and 9. All three stents 22 were held fixed at their positions within the chamber and were rotated about their individual vertical axes during the coating run. The innermost stent was 3 cm from the cathode centerline, the middle stent was 7 cm from the cathode centerline and the outermost stent was 11 cm from the cathode centerline. The deposition was done at a DC power of 2 kW, a Kr pressure of 3.4 mTorr and with the stents biased at −50 V. These are the same conditions used in Run No. 8 in Table 2. All three stents had a matte black appearance and exhibited excellent adhesion when tested. Therefore, stents placed at virtually any radial position within the cathodes and rotating about their individual vertical axes will receive a satisfactory coating, provided they are located between the targets in the axial direction.

An alternative, although less desirable, approach to oblique incidence coatings or large target to substrate distances in order to reduce the energy of the arriving atoms through collisions is to raise the pressure of the sputtering gas.

Sputtering takes place under conditions of continuous gas flow. That is, the sputtering gas is brought into the chamber at a constant rate and is removed from the chamber at the same rate, resulting in a fixed pressure and continuous purging of the gas in the chamber. This flow is needed to remove unwanted gases, such as water vapor, that evolve from the system during coating. These unwanted gases can become incorporated in the growing coating and affect its properties.

The high vacuum pumps used in sputtering, such as diffusion pumps, turbomolecular pumps and cryogenic pumps, are limited with respect to the pressure that they can tolerate at their openings. Therefore, it is well known that in order to achieve high sputtering pressures it is necessary to "throttle" such pumps, or place a restriction in the pump opening that permits the chamber pressure to be significantly higher than the pressure at the pump. Such "throttling" necessarily reduces the flow of gas through the chamber, or gas throughput. Surprisingly, we have found that the adherence of the coatings is improved at high gas throughputs.

In one experiment, a cylindrical magnetron cathode with an inside diameter of 19 cm and length of 10 cm was used to coat a stent with Ta at a sputtering pressure of 30 mTorr in Ar. In order to achieve this pressure, it was necessary to throttle the turbomolecular high vacuum pump on the vacuum system. The Ar flow during this coating was 0.63 Torr-liters per second, corresponding to a throttled pumping speed of 21 liters per second. The stent was placed in the center of the cathode, approximately 9 cm from the target surface. The sputtering power to the cathode was 200 W. According to Westwood's calculations, the average distance a Ta atom travels in Ar at 30 mTorr before reaching thermal velocities is between 1.7 and 3.4 cm, depending on its initial energy. Therefore, these coating conditions should result in a very low-density coating. The black appearance of the coated stent confirmed that this was the case. However, the coating had very poor adhesion.

Figure 11:
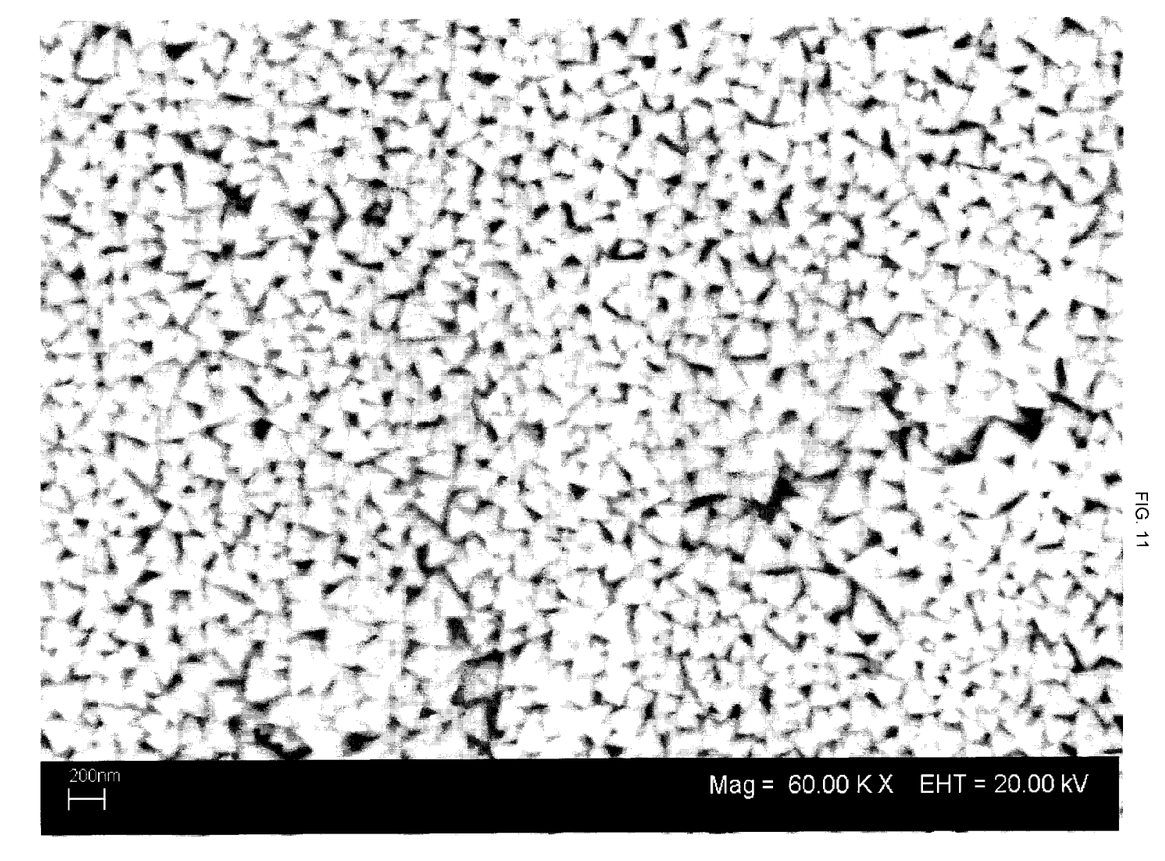
FIG. 11 shows s scanning electron micrograph of the surface of a Ta coating applied to a polished stainless steel surface.

In another experiment, coatings were done on stents in the C position using the 34 cm diameter dual cathode shown in FIGS. 2 and 3. The sputtering gas was Kr at a pressure of 3.4 mTorr. A DC power of 2 kW was used together with a substrate bias of −50 V, the conditions of Run No. 8 in Table 2. The Kr flow was 28 standard cubic centimeters per minute, or 0.36 Torr-liters per second. At a pressure of 3.4 mTorr, this corresponds to a throttled pumping speed of 104 liters per second during the process. The resulting black coatings all flaked at levels between level 1 and level 3 when tested. The position of the pump throttle was then changed and the Kr flow was increased to 200 standard cubic centimeters per minute or 2.53 Torr-liters per second. Coatings were done on stents in the C position at the same power, pressure and bias levels as before. The only difference was that the throttled pumping speed during this process was 744 liters per second. In this case there were no flakes or cracks in the coating evident after testing. A scanning electron micrograph of the surface of a coating applied to a polished stainless steel surface under these conditions is shown in FIG. 11. The open, porous nature of the coating is clearly visible.

Based on the foregoing results, we conclude that adequate adhesion does not result at low gas throughputs, which are usually necessary to achieve high sputtering pressures. The sputtering pressure and system geometry must be chosen together so that the coating flux arrives at the substrate surface either at high angles of incidence or after the sputtered atoms have traveled a sufficient distance from the target to reduce their energies significantly.

Figure 10:
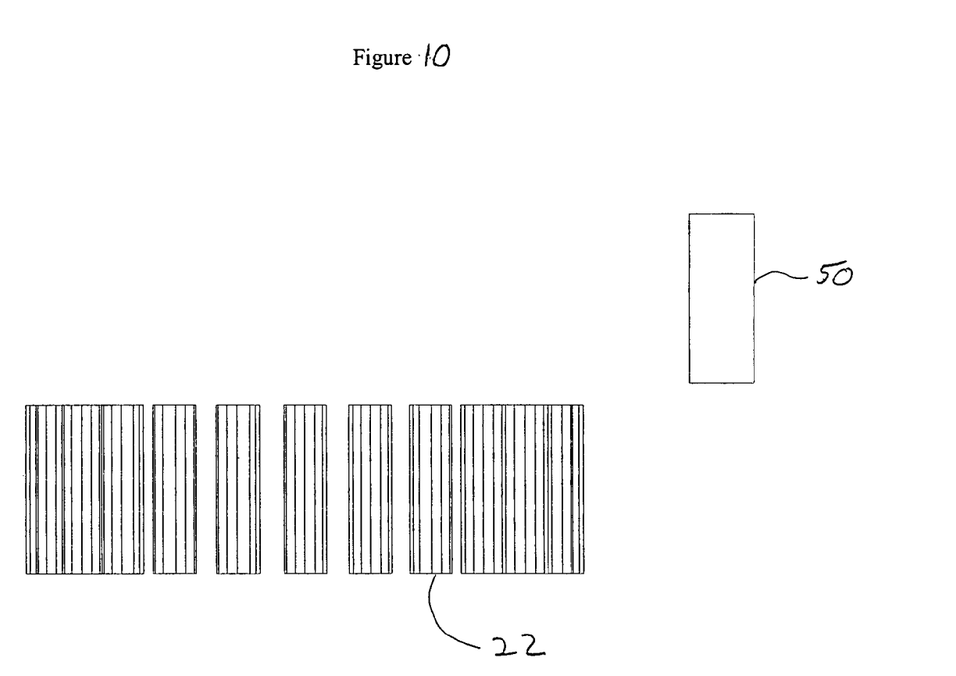
FIG. 10 is a side elevation view of stents positioned beside a planar target at a high angle of incidence.

While the geometry of a cylindrical magnetron makes this possible in an efficient way, as we have shown, the same results can be accomplished using planar targets as well. In the case of planar targets, the requirement is to place the substrates far enough from the target surface(s) that a large target-to-substrate distance is achieved. Alternatively, the substrates could be placed to the side of a planar target so that the material arrives at high incidence angles. This configuration is illustrated in FIG. 10. Of course, the stent positions 22 shown in the case of planar target 50 make inefficient use of the coating material. Nevertheless, FIG. 10 illustrates how the inventive method could be used with geometries other than cylindrical magnetrons.

Although the present invention has been described in considerable detail with reference to certain preferred versions thereof, other versions are possible. For example, a device other than a stent can be coated with Ta or another radiopaque material. Therefore, the spirit and scope of the appended claims should not be limited to the description of the preferred versions contained herein.

All features disclosed in the specification, including the claims, abstract, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. §112.

We claim:

1. An intraluminal medical device for placement within a vascular structure comprising:
   a. a flexible body; and
   b. a porous columnar metallic coating comprising a plurality of independent columnar structures separated from one another by an opening and disposed on at least a portion of the flexible body, wherein
      (i) the porous columnar metallic coating extends in a substantially normal direction from a surface of at least a portion of the flexible body;
      (ii) flaking of the porous columnar metallic coating being less than 1% of the porous columnar metallic coated surface when the flexible body and porous columnar metallic coating are strained up to 8%; and
      (iii) the combination of the size of the columnar structures of the porous columnar metallic coating and the size of the openings between the columnar structures of the porous columnar metallic coating results in an emissivity in the visible spectrum range of at least 80%.

2. The intraluminal medical device of claim 1, wherein the flexible body partially comprises a radio transparent material and
   the porous columnar metallic coating on at least a portion of the flexible body comprises Ta.

3. The intraluminal medical device of claim 2, wherein the porous columnar Ta coating thickness is between approximately 3 and 10 microns.

4. The intraluminal medical device of claim 2, wherein the porous columnar Ta coating is applied to the flexible body by a physical vapor deposition process.

5. The intraluminal medical device of claim 4, wherein the physical vapor deposition process includes one of the group of sputtering, cathodic arc deposition or thermal evaporation.

6. The intraluminal medical device of claim 2 further comprising a material in the porous columnar Ta coating, wherein the material diffuses out over time.

7. The intraluminal medical device of claim 2, wherein the flexible body comprises nitinol.

8. The intraluminal medical device of claim 2, wherein the intraluminal medical device is a stent.

9. The intraluminal medical device of claim 2, wherein the intraluminal medical device is a guide wire.

10. The intraluminal medical device of claim 2, wherein the intraluminal medical device is a catheter.

11. The intraluminal medical device of claim 1, wherein the flexible body further comprises
    an elastic shape retaining body having an outer surface,
    the porous columnar metallic coating is disposed on at least a portion of the outer surface, wherein the porous columnar metallic coating is applied using a physical vapor deposition process.

12. The intraluminal medical device of claim 1, wherein the flexible body further comprises
    a deformable body.

13. The intraluminal medical device of claim 1, wherein the flexible body further comprises an elastic shape retaining body at least partially comprising a material having superelasticity and shape memory.

14. The intraluminal medical device of claim 13, wherein the intraluminal medical device is a stent for use in a biological vessel.

15. The intraluminal medical device of claim 13, wherein the porous columnar metallic coating is a radiopaque coating.

16. The intraluminal medical device of claim 13, wherein the flexible body comprises nitinol.

17. The intraluminal medical device of claim 1, wherein the porous columnar metallic coating is selected from the group consisting of gold, platinum, tantalum, and tungsten.

18. The intraluminal medical device of claim 1, wherein a drug is incorporated into the porous columnar metallic coating.

19. The intraluminal medical device of claim 1, wherein the intraluminal medical device is implantable and further comprises a material in the porous columnar metallic coating that diffuses out over time when implanted.

20. The intraluminal medical device of claim 19, wherein the intraluminal medical device is a stent.

21. The intraluminal medical device of claim 1, wherein the intraluminal medical device is a guide wire.

22. The intraluminal medical device of claim 1, wherein the intraluminal medical device is a stent.

23. The intraluminal medical device of claim 1, wherein the intraluminal medical device is a catheter.

24. An intraluminal medical device for placement within a vascular structure comprising:
    a. a flexible body fabricated from a shape memory alloy having an $A_f$ value below body temperature; and
    b. a porous columnar metallic coating disposed on at least a portion of the flexible body comprising a plurality of independent columnar structures separated from one another by an opening, wherein
       (i) the independent columnar structures extend in a substantially normal direction from a surface of at least a portion of the flexible body;
       (ii) the flexible body and porous columnar metallic coating are operable to withstand strains up to 8%, wherein flaking of the porous columnar metallic coating is less than 1%; and
       (iii) the combination of the sizes of the independent columnar structures of the porous columnar metallic coating and the sizes of the openings between the independent columnar structures results in an emissivity in the visible spectrum range of at least 80%.

25. The intraluminal medical device of claim 24, wherein the shape memory alloy comprises nitinol.

26. The intraluminal medical device of claim 24, wherein the intraluminal medical device further comprises a material disposed within the porous columnar metallic coating, the material diffusing from the porous columnar metallic coating for a period of time after implantation of the intraluminal medical device within the vascular structure.

27. An intraluminal stent, comprising:
 a. a substrate body fabricated from a shape memory alloy, wherein the shape memory alloy comprises first $A_f$ value below body temperature before a porous columnar metallic coating is applied to a surface of at least a portion of the substrate body; and
 b. the porous columnar metallic coating comprising a plurality of independent columnar structures separated from one another by a space, wherein each of the independent columnar structures extend in a substantially normal direction from the surface of at least a portion of the substrate body and the porous columnar metallic coating has an emissivity in the visible spectrum range of at least 80%.

28. The intraluminal stent of claim 27, wherein the intraluminal stent further comprises a material disposed within the porous columnar metallic coating, the material diffusing from the porous columnar metallic coating for a period of time after implantation of the intraluminal stent within a luminal structure.

29. The intraluminal stent of claim 27, wherein flaking of the porous columnar metallic coating is less than 1% when the intraluminal stent is strained up to 8%.

30. The intraluminal stent of claim 27, wherein the shape memory alloy further comprises a second $A_f$ after the porous columnar metallic coating is disposed on the surface of at least a portion of the substrate body, the second $A_f$ is below body temperature.

* * * * *

UNITED STATES PATENT AND TRADEMARK OFFICE
CERTIFICATE OF CORRECTION

| | | |
|---|---|---|
| PATENT NO. | : 8,002,822 B2 | Page 1 of 1 |
| APPLICATION NO. | : 11/087909 | |
| DATED | : August 23, 2011 | |
| INVENTOR(S) | : David A. Glocker | |

It is certified that error appears in the above-identified patent and that said Letters Patent is hereby corrected as shown below:

Claim 27, at Column 13, Line 10: Insert --a-- after the word comprises

Signed and Sealed this
Eighteenth Day of October, 2011

David J. Kappos
*Director of the United States Patent and Trademark Office*